(12) United States Patent
Chuter

(10) Patent No.: US 6,942,691 B1
(45) Date of Patent: Sep. 13, 2005

(54) MODULAR BIFURCATED GRAFT FOR ENDOVASCULAR ANEURYSM REPAIR

(76) Inventor: Timothy A. M. Chuter, 2209 Adeline Dr., Burlingame, CA (US) 94010

( * ) Notice: Subject to any disclaimer, the term of this patent is extended or adjusted under 35 U.S.C. 154(b) by 0 days.

(21) Appl. No.: 09/560,012

(22) Filed: Apr. 27, 2000

(51) Int. Cl.[7] .................................................. A61F 2/06
(52) U.S. Cl. ..................................... 623/1.35; 623/1.16
(58) Field of Search .............................. 623/1.35, 1.36, 623/1.44, 1.15, 1.16

(56) References Cited

U.S. PATENT DOCUMENTS

| | | | |
|---|---|---|---|
| 5,064,435 A | 11/1991 | Porter | |
| 5,104,399 A | * 4/1992 | Lazarus | ........................ 623/1 |
| 5,316,023 A | 5/1994 | Palmaz et al. | |
| 5,562,724 A | 10/1996 | Vorwerk et al. | |
| 5,571,170 A | 11/1996 | Palmaz et al. | |
| 5,575,817 A | 11/1996 | Martin | |
| 5,591,228 A | 1/1997 | Edoga | |
| 5,609,605 A | 3/1997 | Marshall et al. | |
| 5,609,627 A | 3/1997 | Goicoechea et al. | |
| 5,632,763 A | 5/1997 | Glastra | |
| 5,632,772 A | 5/1997 | Alcime et al. | |
| 5,639,278 A | 6/1997 | Dereume et al. | |
| 5,653,743 A | 8/1997 | Martin | |
| 5,662,675 A | 9/1997 | Polanskyj Stockert et al. | |
| 5,676,696 A | 10/1997 | Marcade | |
| 5,676,697 A | 10/1997 | McDonald | |
| 5,683,449 A | 11/1997 | Marcade | |
| 5,683,450 A | 11/1997 | Goicoechea et al. | |
| 5,683,451 A | 11/1997 | Lenker | |
| 5,683,453 A | 11/1997 | Palmaz | |
| 5,693,086 A | 12/1997 | Goicoechea et al. | |
| 5,693,088 A | * 12/1997 | Lazarus | ........................ 623/1 |
| 5,695,517 A | 12/1997 | Marin et al. | |
| 5,709,713 A | 1/1998 | Evans et al. | |
| 5,713,917 A | 2/1998 | Leonhardt et al. | |
| 5,718,724 A | 2/1998 | Goicoechea et al. | |
| 5,755,734 A | 5/1998 | Richter et al. | |
| 5,755,735 A | 5/1998 | Richter et al. | |
| 5,755,770 A | 5/1998 | Ravenscroft | |
| 5,755,772 A | 5/1998 | Evans et al. | |
| 5,755,773 A | 5/1998 | Evans et al. | |
| 5,769,882 A | * 6/1998 | Fogarty et al. | ................. 623/1 |
| 5,776,180 A | 7/1998 | Goicoechea et al. | |
| 5,800,508 A | 9/1998 | Goicoechea et al. | |
| 5,824,036 A | 10/1998 | Lauterjung | |
| 5,824,037 A | 10/1998 | Fogarty et al. | |
| 5,824,040 A | 10/1998 | Cox et al. | |
| 5,824,042 A | 10/1998 | Lombardi et al. | |
| 5,827,310 A | 10/1998 | Marin et al. | |
| 5,843,158 A | 12/1998 | Lenker et al. | |
| 5,843,160 A | 12/1998 | Rhodes | |
| 5,855,598 A | 1/1999 | Pinchuk | |
| 5,871,536 A | 2/1999 | Lazarus | |
| 5,916,263 A | 6/1999 | Goicoechea et al. | |
| 5,938,696 A | 8/1999 | Goicoechea et al. | |

(Continued)

FOREIGN PATENT DOCUMENTS

FR   2 748 197 A1   11/1997

Primary Examiner—Bruce Snow
(74) Attorney, Agent, or Firm—William G. Lane

(57) ABSTRACT

The present invention is a bifurcated modular graft for repairing body lumens. In one embodiment, the graft includes two elements, each element being fabricated from material which is flexible. The first element embodies a tubular docking section which bifurcates into left and right tubular limbs. The first element is adapted to be inserted into vasculature of a patient so that the device spans and is supported by a point of bifurcation. The second element is made from a single tubular segment and is adapted to engage the docking section of the first element. The first and second elements are sealed to each other and within the vasculature by expanding support structures.

10 Claims, 9 Drawing Sheets

U.S. PATENT DOCUMENTS

| | | |
|---|---|---|
| 5,948,017 A | 9/1999 | Taheri |
| 5,961,548 A | 10/1999 | Shmulewitz |
| 5,984,955 A | 11/1999 | Wisselink |
| 5,993,481 A | 11/1999 | Marcade et al. |
| 6,015,431 A | 1/2000 | Thornton et al. |
| 6,033,434 A | 3/2000 | Borghi |
| 6,033,435 A | 3/2000 | Penn et al. |
| 6,036,723 A | 3/2000 | Anidjar et al. |
| 6,051,020 A | 4/2000 | Goicoechea et al. |
| 6,099,558 A | 8/2000 | White et al. |
| 6,102,938 A | 8/2000 | Evans et al. |
| 6,117,167 A | 9/2000 | Goicoechea et al. |
| 6,123,722 A | 9/2000 | Fogarty et al. |
| 6,149,682 A | 11/2000 | Frid |
| 6,152,956 A * | 11/2000 | Pierce ....................... 623/1.13 |
| 6,165,214 A * | 12/2000 | Lazarus ..................... 623/1.35 |
| 6,695,875 B2 | 2/2004 | Stelter et al. |

* cited by examiner

MODULAR BIFURCATED GRAFT FOR ENDOVASCULAR ANEURYSM REPAIR

BACKGROUND OF THE INVENTION

The present invention relates to intraluminal grafts which are used for repairing defects in vessels and other lumens within the body. More particularly, the present invention relates to methods and systems for the endovascular repair of a defect using a flexible bifurcated modular graft.

Aneurysms are discrete dilations of the arterial wall. One of the most common, and among the most life threatening, is an aneurysm of the abdominal aorta between the renal and iliac arteries. If untreated, the aneurysm dilates progressively with an ever increasing risk of rupture and hemorrhagic death.

One method of treatment is provided by direct surgical intervention, in which the defective vessel may be bypassed or replaced using a prosthetic device such as a synthetic graft. The risks involved in direct surgical intervention of this magnitude are great, and include an extensive recovery period.

In recent years, a less invasive method of treatment has evolved through a series of inventions. The details vary, but, conventionally, a resilient tubular conduit fashioned from flexible fabric (herein referred to as a "graft") is introduced into the defective vessel by means of catheters introduced into the femoral artery. The graft is attached to the non-dilated arteries above and below the aneurysm using expandable metallic cylinders (herein referred to as "support structures").

Many abdominal aortic aneurysms extend to the aortic bifurcation, with the result that there may be no healthy vascular tissue at the lower end of the aorta, making it impractical to attach the lower end of the graft to the aortic wall. Accordingly, most cases of endovascular aneurysm repair employ a graft having a bifurcated shape, with a trunk portion and two limbs, each limb extending into an iliac artery where healthy tissue can be found for attaching the graft.

Bifurcated grafts may take one of two forms, depending on the method of insertion. Either the graft is inserted as a single element (unibody form), or it may be made up from more than one modular element which are assembled in vivo within the patient (modular form). Unibody grafts are positioned using a combination of catheters. In many of the current systems, orientation may be difficult to control, and twisting can occur. Moreover, the graft enters the patient having a fixed length based on preoperative sizing of the patient's vasculature. Thus, any error in preoperative sizing of the patient's vasculature may result in one or more orifice of the graft being incorrectly positioned.

Modular bifurcated grafts may overcome these difficulties. The insertion of a modular bifurcated graft conventionally commences with the insertion and positioning of a bifurcated trunk element of the graft within the aorta. Thereafter, up to two tubular limb elements may be inserted, being positioned to extend from orifices in the bottom of the trunk element to a certain distance within the iliac arteries. Each tubular limb is connected to the trunk element by means of a joint, which may be formed with the assistance of expandable support structures which are implanted at a point of overlap between trunk and limb elements and which, when expanded, form a pressure seal between the limb element and the trunk element. The staged insertion of the graft in modular elements as described above may reduce problems associated with orientation and twisting of the graft. It may also reduce problems associated with achieving the correct length of the graft, because it may be possible to customize the final length of the graft in vivo by varying the length of the overlap between the trunk and the limb elements. By using various size limb elements, the diameter of the flow path defined by the modular bifurcated graft also may be customized.

However, insertion of bifurcated grafts in modular form as described above may be attended by additional complications. The most troubling long-term complication is the disruption of a joint between the trunk and a limb element, which may be caused by vascular movement or forces generated by downstream fluid flow. Where the limb elements are individually added to the trunk element, there may be no mechanical restraint, other than the support structures, restraining the limb elements from downward movement. Thus, should the support structure holding the limb element in contact with the trunk element fail to operate as intended, due to excessive force or deformation of the support structure, extensive downward migration of the limb elements may result. Moreover, conventional methods used to form joints between elements of a modular bifurcated graft may result in an inadequate joint if insufficient overlap is provided between the elements, or if the elements are too rigid to accommodate unanticipated vasculature geometry.

Accordingly, there exists a need for an improved modular bifurcated graft that embodies robust junctions between modular elements thereof as well as structure which can accommodate a wide range of geometries. This invention addresses these and other needs.

SUMMARY OF THE INVENTION

Briefly, and in general terms, the modular graft of the present invention embodies structure that derives mechanical support from the anatomy into which the graft is implanted. The modular graft includes elements which are configured to overlap to an extent sufficient to create a robust seal. The graft is additionally adapted to be sufficiently flexible to accommodate awkward geometry.

The graft of the present invention is contemplated to be assembled in vivo using first and second modular elements, each of which is adapted to be expandable from a compressed condition to an expanded condition. In one preferred embodiment, support structures are employed to cause the first and second modular elements to sealingly engage walls of vasculature.

The first element is contemplated to have a bifurcated profile, with a tubular docking section adapted to extend into a main artery, and left and right tubular limbs each adapted to individually occupy a length of arteries branching from the main artery, respectively. A first support structure is connected to the docking section, a second support structure is connected to the left limb, and a third support structure is connected to the right limb. Each support structure is adapted to expand from a compressed condition to an expanded condition.

The second element is contemplated to occupy the main artery and to overlap with the docking section. Additional support structures may be connected to the second element for facilitating implantation at a repair site.

In a preferred method of in vivo assembly, the first element is inserted within the vasculature of a patient in a compressed condition, and is activated to assume an expanded condition so that the first element spans and is supported by a point of bifurcation in the vasculature. The second tubular element is thereafter inserted into the vasculature in a compressed condition. The second element is positioned so that, upon expansion, one end thereof is attached to the main artery wall and another end thereof, is positioned into engagement with the docking section of the first element. In a preferred embodiment, an overlapping engagement is contemplated such that a portion of a superior component is placed within an inferior component to thereby advantageously facilitate routing flow past a point of origin of the overlap. A sealing stent can subsequently be placed at the overlap to enhance the seal of one component to another.

By installing the modular bifurcated graft in stages using separate elements in the above manner, problems associated with orientation of the graft may be reduced. Moreover, by configuring the first element to span across the point of bifurcation of the main artery, mechanical resistance to downstream migration of the graft is achieved. Furthermore, the bottom-up assembly of the components of the present invention and the contemplated overlapping engagement cooperate to lower the likelihood of an endoleak. Significantly, the flexible quality of the first and second elements and the continuous overlapping joint therebetween allow the graft to conform to a wide range of vascular geometries as well as to accommodate movement of the vasculature after implantation without disrupting the seal formed between the elements of the graft and the vasculature.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

The present invention is described in the context of providing a device and method for repair of body lumens using a graft assembly. While the description which follows relates to the preferred use of the invention, namely, the repair of the aorta of a patient, the invention may equally be applied to any defective bifurcated vessel of a patient. The terms "superior" and "inferior" as used herein shall mean upstream and downstream respectively. The preferred embodiments of the system and method of the present invention are described below.

Figure 1:
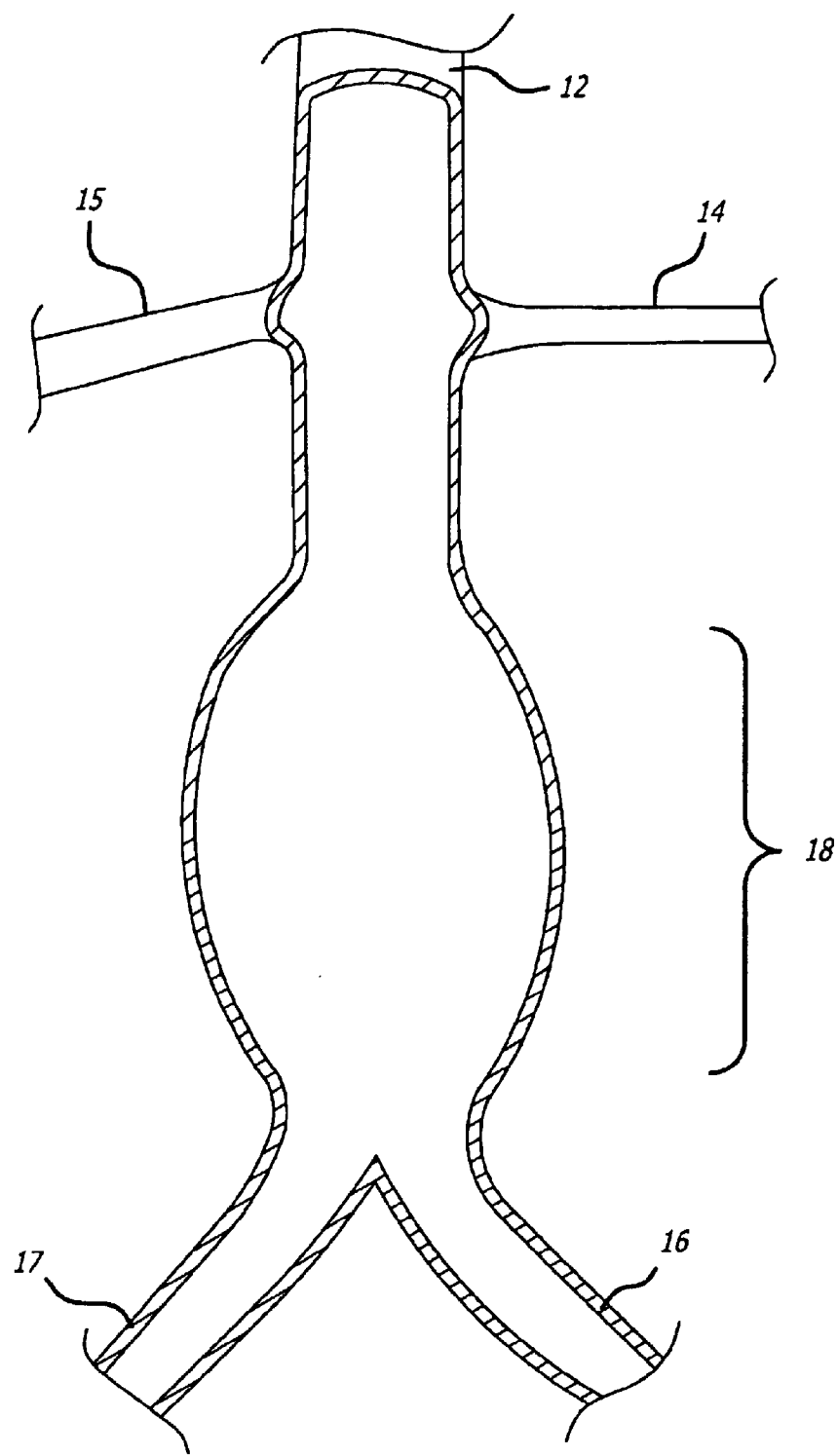
FIG. 1 is a cross-sectional view, depicting a portion of vasculature of a patient.

A site for the potential use of the present invention is exemplified in FIG. 1, which is a schematic depiction of the vascular system of a patient showing the relationship of the aorta 12 to the left and right renal arteries 14, 15 and the left and right iliac arteries 16, 17 and also showing a diseased portion 18 of the aorta below the renal arteries dilated by an aneurysm. (Left and right are described as from the viewpoint of the patient and are thus inverted from the viewpoint of the reader.)

Figure 2:
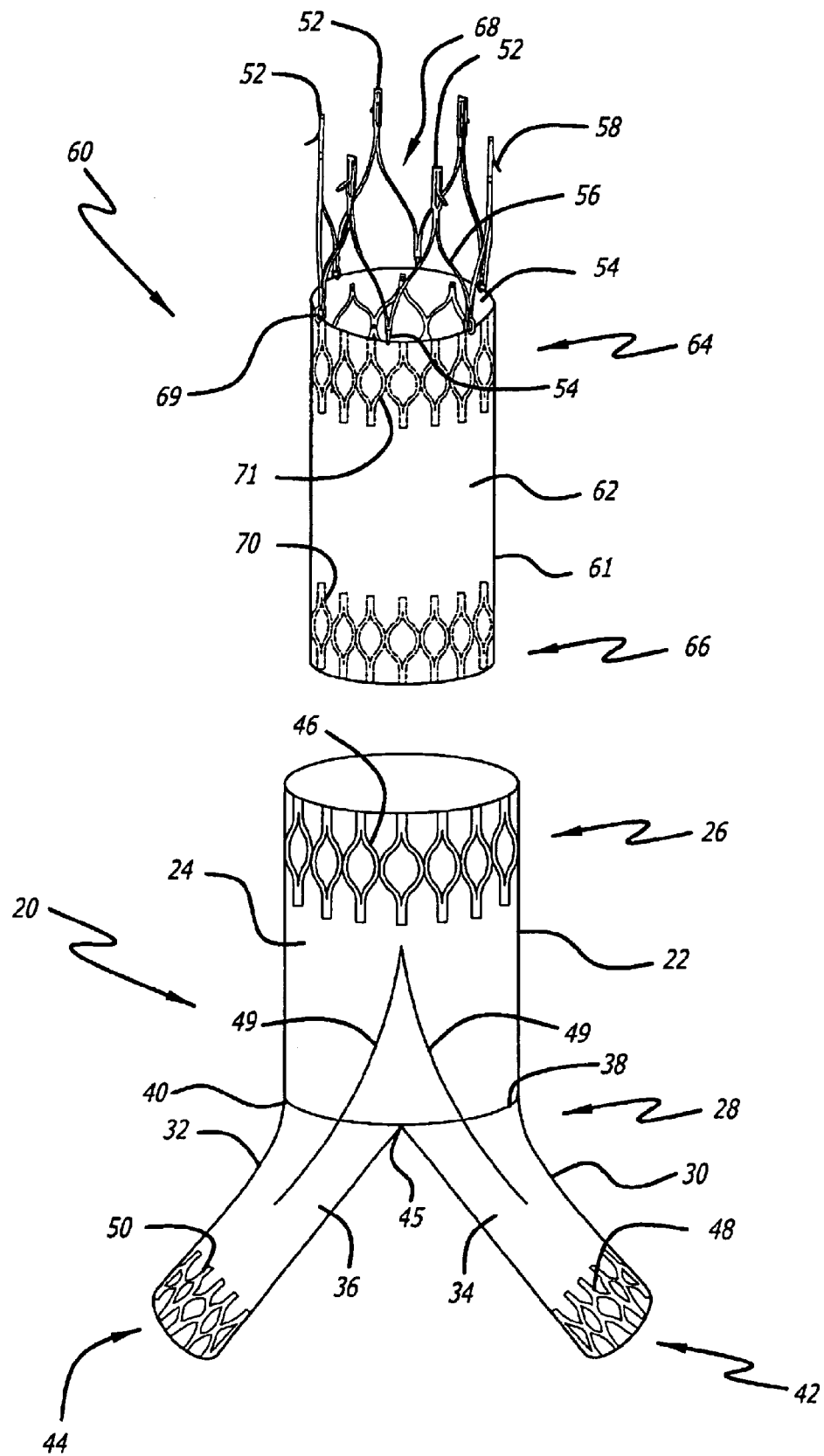
FIG. 2 is a perspective view, depicting one embodiment of the modular bifurcated graft of the present invention.

In accordance with one embodiment of the modular graft of the present invention, exemplified in FIG. 2, a first element 20 and a second element 60 of a modular bifurcated graft are assembled before insertion into the patient's vascular system. The first element 20 includes a tubular docking section 22 having a continuous wall 24 between a superior end 26 and an inferior end 28 defining a lumen and is adapted to be expanded from a collapsed condition to an expanded condition. Protruding from the inferior end of the docking section are a left limb 30 and a right limb 32, each having a continuous wall 34, 36 between superior ends 38, 40 and inferior ends 42, 44 respectively, defining lumens and being adapted to be expanded from a collapsed condition to an expanded condition. At a point of connection between the left limb 30 and right limb 40 is a graft bifurcation junction 45. The wall 24 of the docking section 22 is continuously connected with the walls 34, 36 of the left limb and the right limb, to define a bifurcated lumen of the first element 20. The docking section 22 and limbs 34, 36 of the first element 20 may be manufactured from any flexible surgical implantable material such as Dacron™ which is known to be sufficiently biologically inert, non-biodegradable, and durable. One material found to be satisfactory is DeBakey soft woven Dacron™ vascular prosthesis (uncrimped) sold by USCI.

As further exemplified in FIG. 2, the first element 20 may include a plurality of support structures. A first support structure 46 is positioned on the wall 24 of the docking section 22 at the superior end 26 thereof. A second support structure 48 is positioned on the wall 34 of the left limb 30 at the inferior end 42 thereof. A third support structure 50 is positioned on the wall 36 at the inferior end 44 of the right limb 32. Each of the support structures 46, 48, 50 are configured to maintain the patency of the bifurcated lumen of the first element 20. In a preferred aspect, the support structures 46, 48, 50 may be positioned on the outside wall of the first element 20, although in other aspects one or more of them may be positioned on the inside wall. The support structures 46, 48, 50 may be connected to the wall of the first element 30 by suitable means, such as Dacron™ polyester suture material. In a variation of this embodiment, bracing wires 49 may be connected to the wall of the first element 30 to extend between the first support structure 46 and second support structure 48 and also between first support structure 46 and third support structure 50, to support the bifurcated lumen of the first element 30. In yet a further variation, additional support structures (not shown) may be added for the same purpose.

The second element 60 includes a tubular segment 61 having a continuous wall 62 between a superior end 64 and an inferior end 66 defining a lumen adapted to be expandable from a collapsed condition to an expanded condition, and may be made from the same flexible biocompatible material as the docking section 22 and limbs 30, 32 of the first element 20. A fourth support structure 68 may be connected to the superior end 64 and a fifth support structure 70 may be connected to the inferior end 66 of the tubular segment 61. In alternative embodiments, additional support structures may be added, as required, in the space between the fourth 68 and fifth 70 support structures, as may be required. For example, a sixth support structure 71 is shown attached to the inner lumen of the tubular segment 61 adjacent to its superior end 64.

Figure 7:
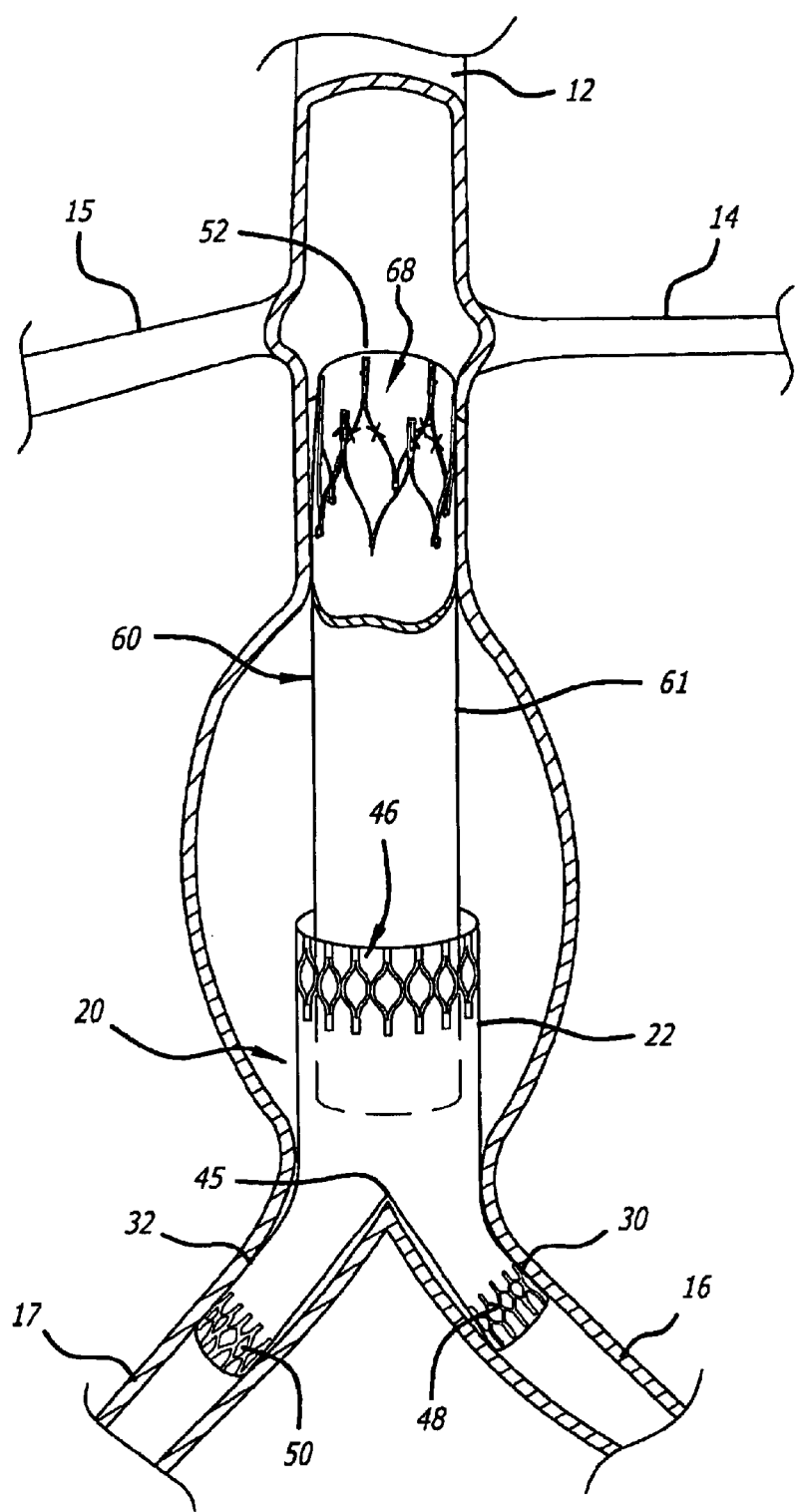
FIG. 7 is a partial cross-sectional view, depicting an alternative embodiment of a second element implanted within vasculature.

In one embodiment of the second element 60, exemplified in FIG. 2, the fourth support structure 68 may be longitudinally separated from the tubular segment 61, but connected to its superior end 64 by a plurality of ties 69 which may be made from any flexible substance which is durable and biocompatible. For example, Dacron™ polyester suture material has been found to be suitable. The ties 69 may be configured to loop around the superior elements forming the support structure 68, and to penetrate the wall of the tubular segment, or may be given any other suitable configuration to form a connection between support structure 68 and tubular segment 61. In this embodiment, the fourth support structure 68 operates dominantly to fix the tubular segment to the aortic wall 12, and to prevent migration thereof. However, it is not essential to the present invention that the fourth support structure 68 be longitudinally separated from the tubular segment 61. In an alternative embodiment of the second element 60, exemplified in FIG. 7, the fourth support structure 68 may be positioned substantially within the lumen of the tubular segment 61 and may operate to both anchor the tubular segment 61 against inferior migration and to form a seal between the tubular segment 61 and the aortic wall 12.

In a preferred embodiment, the support structures used in the present invention are self-expanding. In other embodiments the support structures may be balloon expanded. In a preferred configuration, each self-expanding support structure used in the present invention may be manufactured from a continuous cylinder, into which a pattern may be cut by a laser or by chemical etching to produce slits in the wall of the cylinder. The resulting structure may thereafter be stretched and annealed to give it a desired final configuration. The preferred final configuration includes a shape which undulates between superior apices 52 and inferior apices 54 which are joined by connecting legs 56, as is exemplified in FIG. 2, the same being suitable for the configuration of the fourth support structure 68. In this configuration, when the support structure 68 is compressed, its legs 56 and apices 52, 54 are urged radially outward in a direction generally at right angles to its axis. In another aspect, the support structure may be modified by joining its mirror image (taken about a line perpendicular to its axis) to its superior end, thus providing a "closed cell" configuration, such as support structure 46. Where such a support structure is intended to anchor the graft against migration, as is the case with the fourth support structure 68, hooks 58 may be added to enhance this function. Preferably, the self-expanding support structures are made from a material having highly elastic properties such as nickel-titanium alloys, including Nitinol, since the same allows a great amount of expansion and compression of structures without permanent deformation. Implantable stainless steel is also known to be satisfactory for the purpose. An additional material from which such support structure may be manufactured is Elgiloy™ which is a chromium-cobalt-nickel alloy manufactured and sold by Elgiloy of Elgin, Ill.

Figure 3:
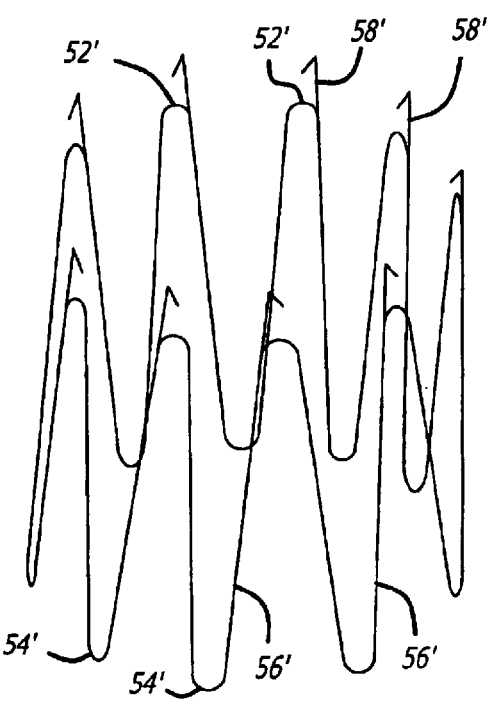
FIG. 3 is a perspective view, depicting an alternative embodiment of a support structure.

In an alternative aspect, as exemplified in FIG. 3, the self-expanding support structures used in the present invention may be formed from wire which follows a generally undulating path within a generally cylindrical profile, producing a plurality of alternating superior apices 52' and inferior apices 54' which are joined by connecting legs 56'. When the support structure is compressed, its legs and apices are urged radially outward in a direction generally at right angles to its axis. As in the previously described aspect, hooks 58' may be connected to the support structure to enhance its ability to attach the graft to the vascular wall if necessary.

It is to be recognized that balloon expanded support structures may be used in alternative embodiments. Methods for deploying such structures are known in the art.

Figure 4:
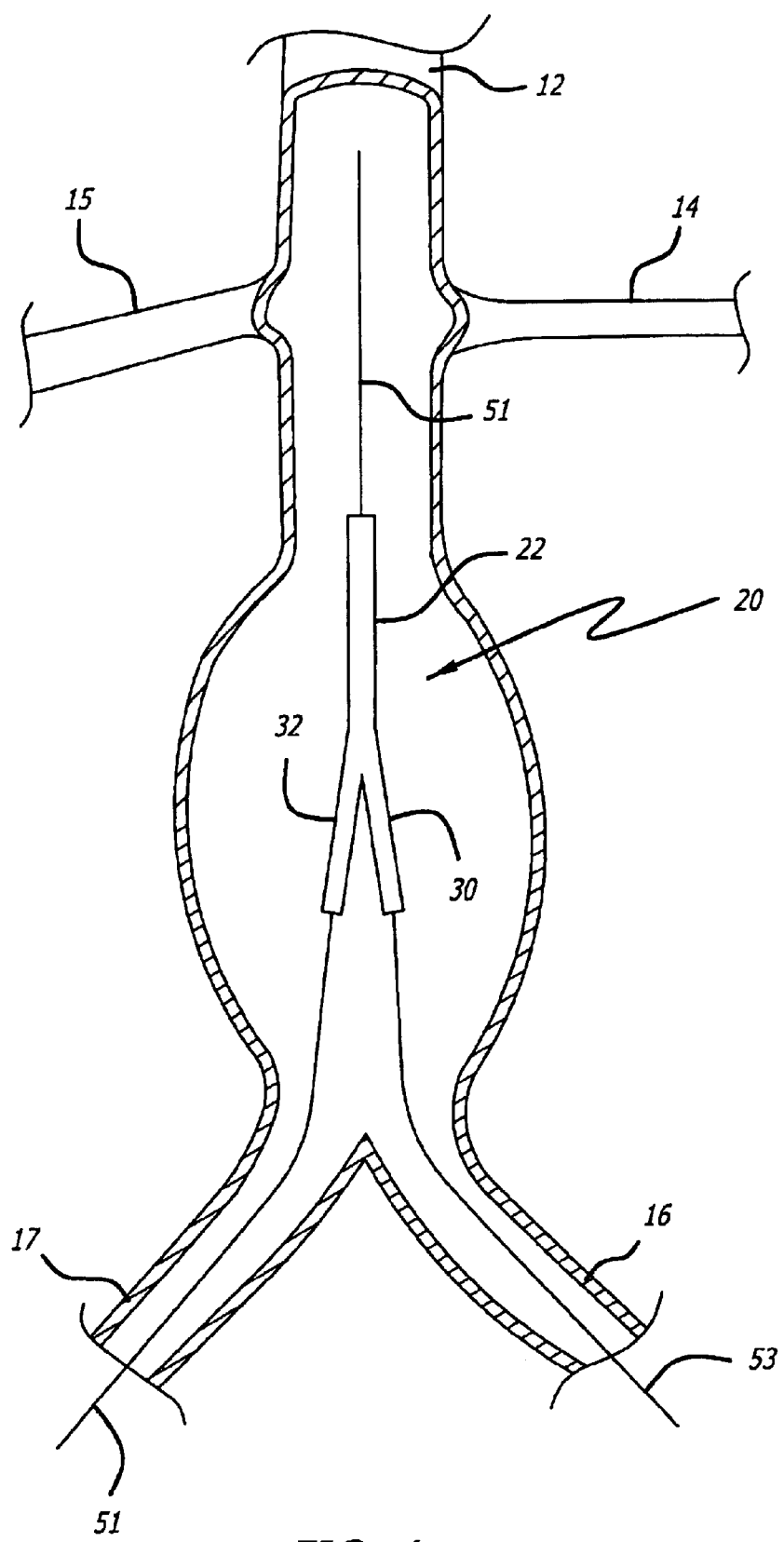
FIG. 4 is a partial cross-sectional view, depicting a first stage of implantation of a first element of the present invention.

Once the first element 20 and the second element 60 are configured as set forth above, the first element 20 is placed in a delivery capsule (not shown) in compressed condition and inserted over a guide-wire into the vasculature from an opening in the femoral artery (not shown). Methods of inserting a bifurcated graft element with expandable support structures into the patient's vasculature so as to span the iliac arteries 16, 17 are complicated and require skillful operation, but are well known in the art. FIG. 4 exemplifies in principle how it is necessary to pass the first element 20 in a compressed condition proximally into the aorta over a guidewire 51, before withdrawing the two limbs 30, 32 distally into the iliac arteries 16, 17. In order to withdraw the left limb 30 into the left iliac artery 16, it may be necessary to insert a second guide-wire 53 from an opening (not shown) in the left femoral artery to gain control of the right limb and manipulate it into place.

Figure 5:
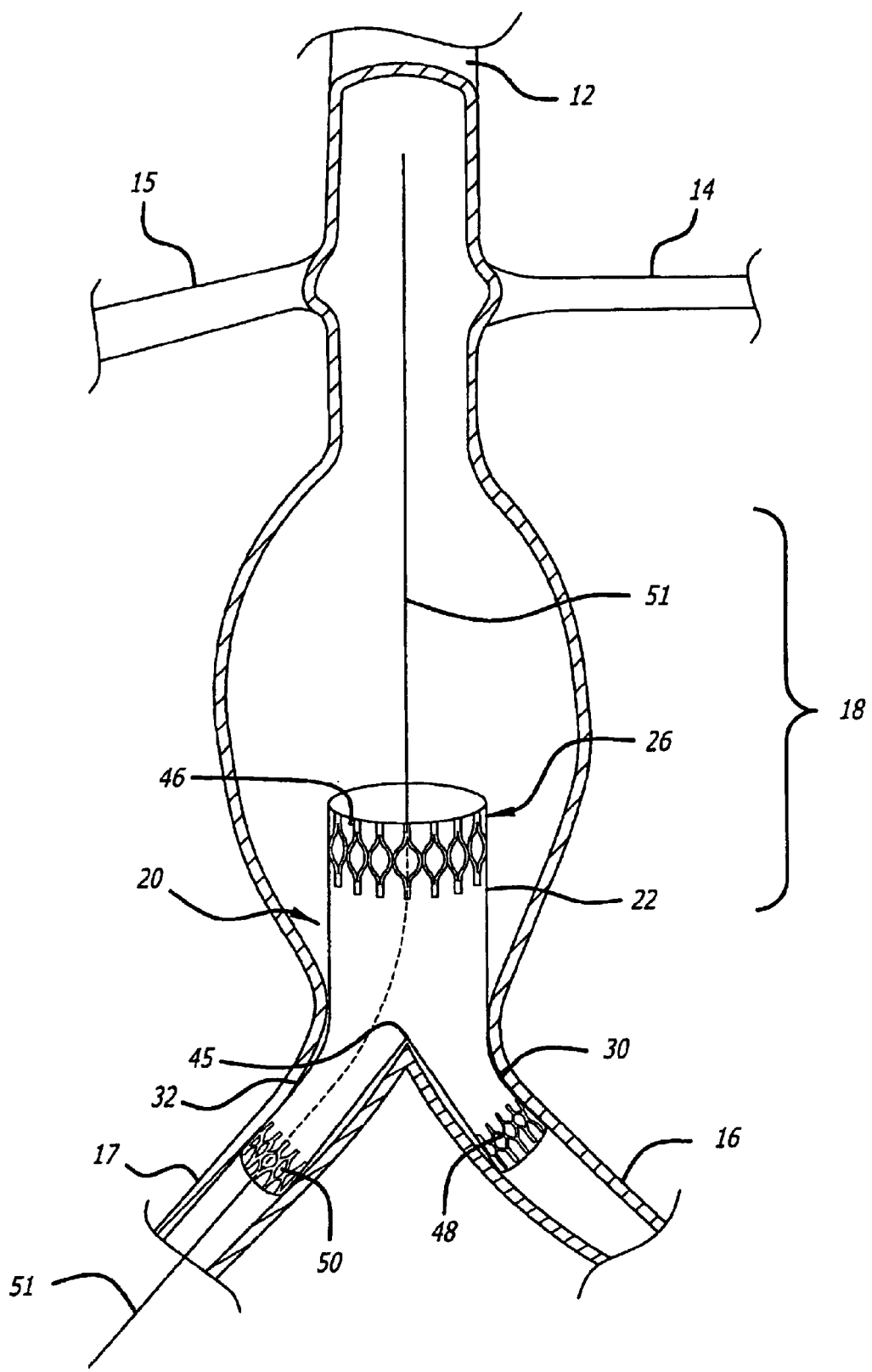
FIG. 5 is a partial cross-sectional view, depicting a second stage of implantation of the device shown in FIG. 4.

Upon deployment of the first element 20, as exemplified in FIG. 5, the left and right limbs 30, 32 occupy a length of the left and right iliac arteries 16, 17 respectively, with the second and third support structures 48, 50 being adapted to expand and to compress the walls of the left and right limbs against the walls of the left and right iliac arteries respectively. The graft bifurcation junction 45 is advantageously placed in close proximity to the bifurcation point of the vascular to thereby derive mechanical support therefrom or from the legs in the iliacs. The docking section 22 is configured to extend into the aorta 12 and expanded at its superior end 26 by the first support structure 46. The first guide-wire 51 is left in place within the vasculature, and is adapted to extend from the opening in the right femoral artery through the lumen of the first element 20 and to extend proximally into the aorta 12.

Figure 10:
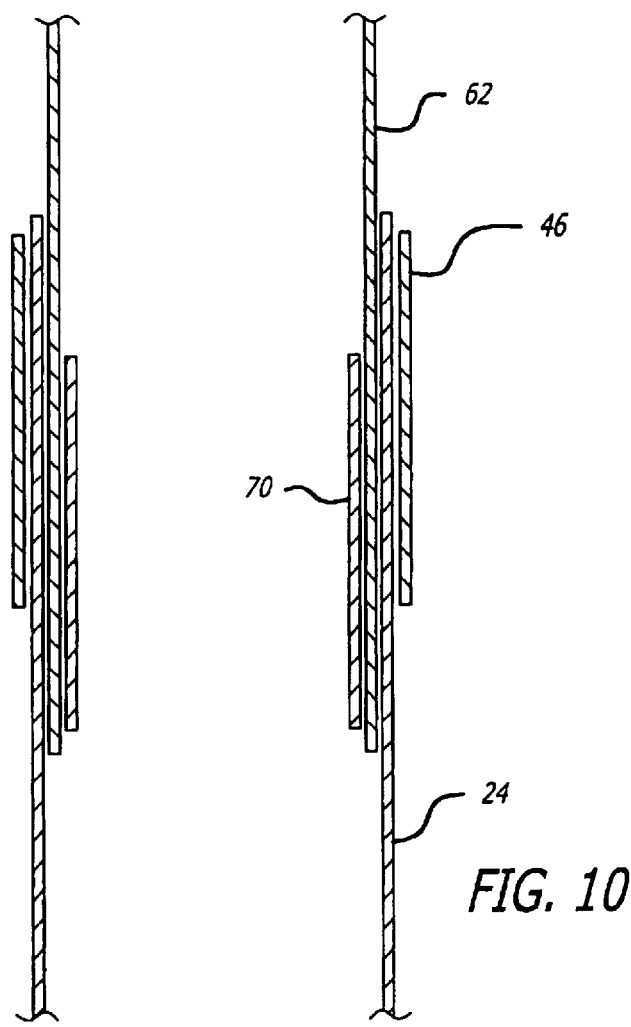
FIG. 10 is a cross-sectional view taken along line A—A of FIG. 6.
Figure 6:
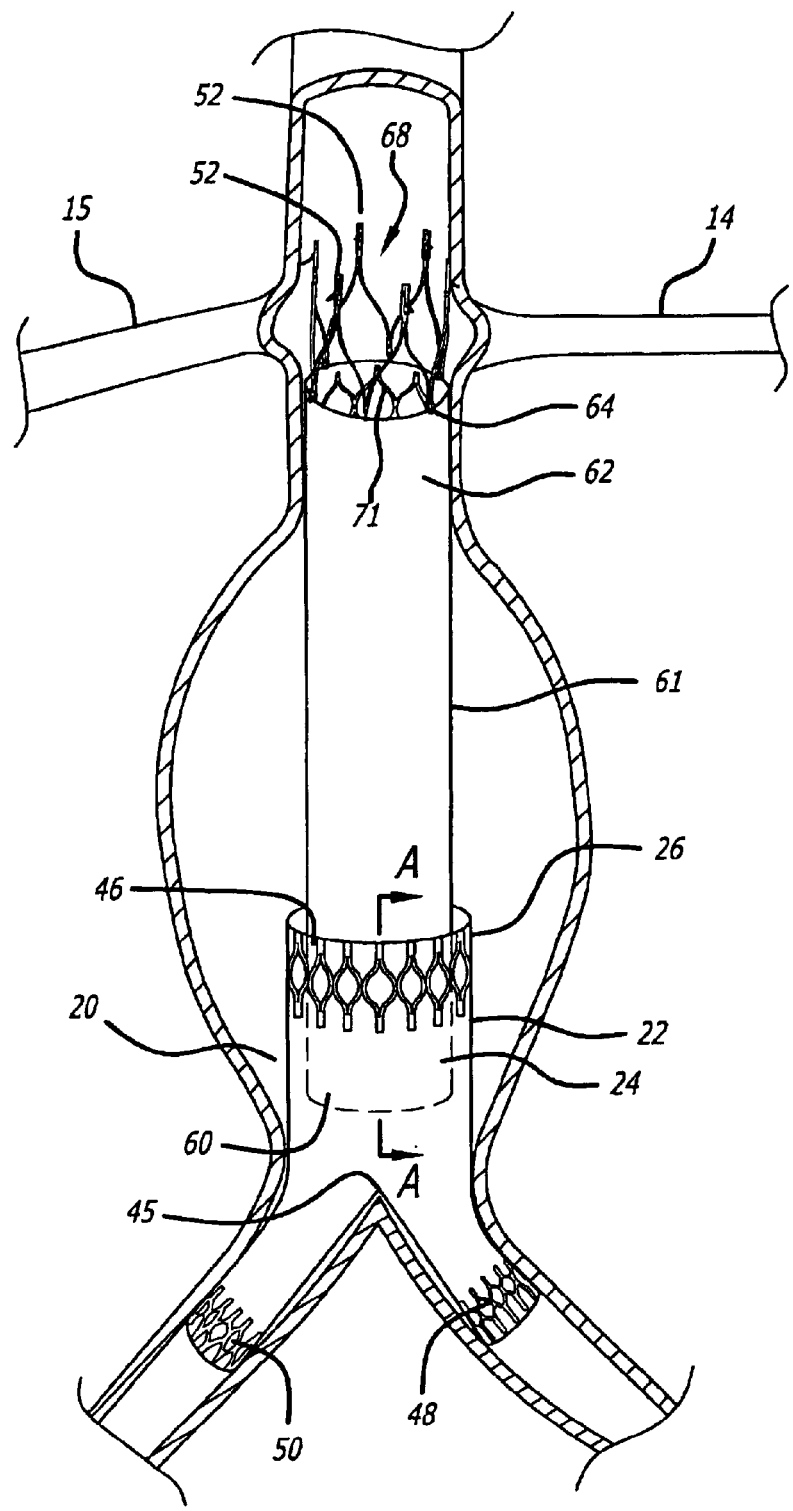
FIG. 6 is a partial cross-sectional view, depicting a second element implanted with vasculature.

After deployment of the first element 20, the second element 60 is loaded into a delivery capsule (not shown) in compressed condition, and is passed over the first guide-wire 51 until it extends into the aorta 12, whereupon it is released from the delivery capsule to assume its expanded condition. As exemplified in FIG. 6, the second element 60 in its expanded condition is positioned so that the wall 62 of the tubular segment 61 is compressed at its superior end 64 into contact with the aortic wall 12. The fourth support system 68 anchors the tubular segment 61 against migration, and may contribute to a seal being formed between the tubular segment 61 and the aortic wall 12. Preferably, a sixth support structure 71 may be attached to the lumen of the tubular section at its superior end 64 to enhance the seal. In another embodiment of the second element 20, previously described and exemplified in FIG. 7, the fourth support structure 68 is positioned substantially within the lumen of the tubular segment 61, allowing the fourth support structure 68 to play a more significant role in forming a seal between the tubular segment 61 and the aortic wall 12. If hooks 52 are attached to the fourth support structure 68, they may be configured to protrude over the superior end 64 of the tubular segment 61 to engage with the aorta 12, or they may be adapted to protrude through the wall of the tubular segment 61. In either embodiment, the inferior end 66 of the tubular segment 61 is compressed into contact with the inner wall 24 of the docking section 22 by the fifth support structure (not shown in FIG. 6 but exemplified in FIG. 2 and in section in FIG. 10). The diameter of the tubular segment 61 may vary from its superior end 64 to its inferior end 66, but in the expanded condition the diameter of the superior end 64 must be slightly larger than the aortic neck 12 to which it is to be attached, and the diameter of the inferior end 66 must be slightly larger than the diameter of the lumen of the docking section 22 to which it is to be attached. It will be appreciated that in the event that the material of the first 20 and second 60 elements is not elastically expansible, and that if the diameter of an element is smaller than the diameter of the lumen to which it is to be attached, a proper fluid seal cannot be formed.

When fully deployed, the modular graft of the present invention allows the first element 20 to derive mechanical support against inferior-directed forces by resting on the point of bifurcation of the aorta 12 or by being very close thereto such that legs in iliacs provide support. A support wire 49 in the first element 20 could provide such support. Accordingly, the second and third support structures 48, 50 implanted in the inferior ends 42, 44 of the left and right limbs 30, 32 are adapted to keep those limbs in fluid seal with the left and right iliac arteries 16, 17 but are not necessarily adapted to provide, but can provide a resistance to inferior migration of the first element 20. Likewise, the first support structure 50 at the docking section's superior end 24 is adapted to hold that end open, but not necessarily to provide an anchor against inferior migration of the first element.

It will be further appreciated that the present invention permits a continuous overlapping seal to be formed over the length of the docking section 22, joining the first element 20 to the second element 60. The interior lumen of the docking section 22 is long enough to permit a significant overlap with the lumen of the second element 60, yet is short enough to eliminate the problems of orientation or twisting during implantation associated with a unibody bifurcated graft. Significantly, the overlapping arrangement presents a profile that advantageously routes blood flow beyond the most superior point of overlap between the first 20 and second elements 60 to thereby facilitate providing an effective seal. In a preferred embodiment, the length of the docking section 22 may be up to about 25 mm and to 75 mm or more. Additionally, the present invention allows that an error in pre-operative sizing of the length of the vasculature may be accommodated by taking up the error in the overlap between the tubular segment 61 and the docking section 22. Thus, if it is found that the superior end 64 of the tubular segment 61 should be attached to the aortic neck 12 at a point lower than that anticipated by pre-operative measurement, the length of the overlap between second element 60 and docking section 22 may be increased by the same difference, thus allowing attachment of the superior end 64 of the second element 60 to take place at the optimal position on the aortic neck 12, and yet to maintain the existence of the fluid seal between the first element 20 and the second element 60. Moreover, the strategic placement of support structures at the overlap between the first 20 and second 60 elements aids in creating an effective seal by urging the first element 20 against the second element 60.

Figure 8:
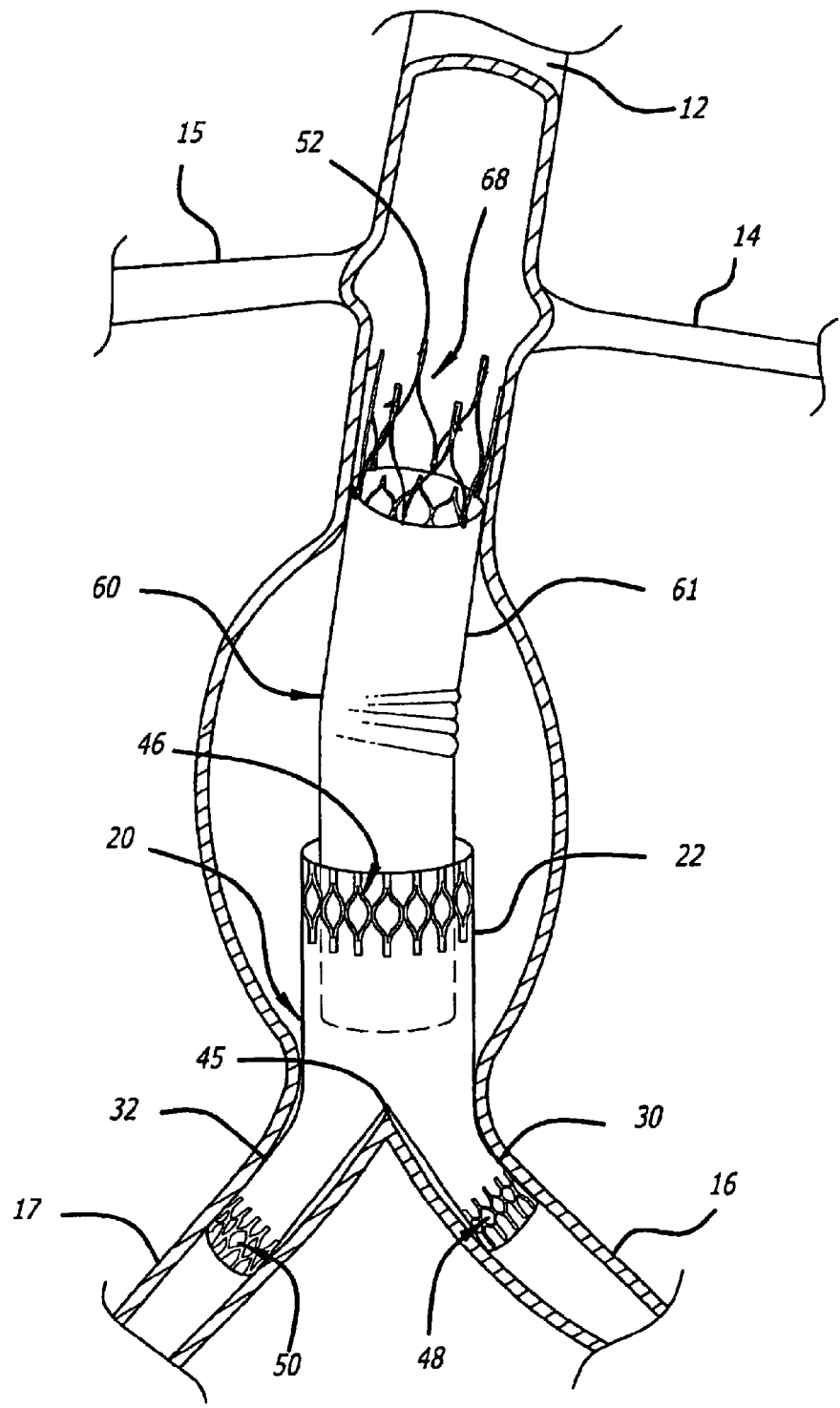
FIG. 8 is a partial cross-sectional view, showing the ends of the second element out of axial alignment.
Figure 9:
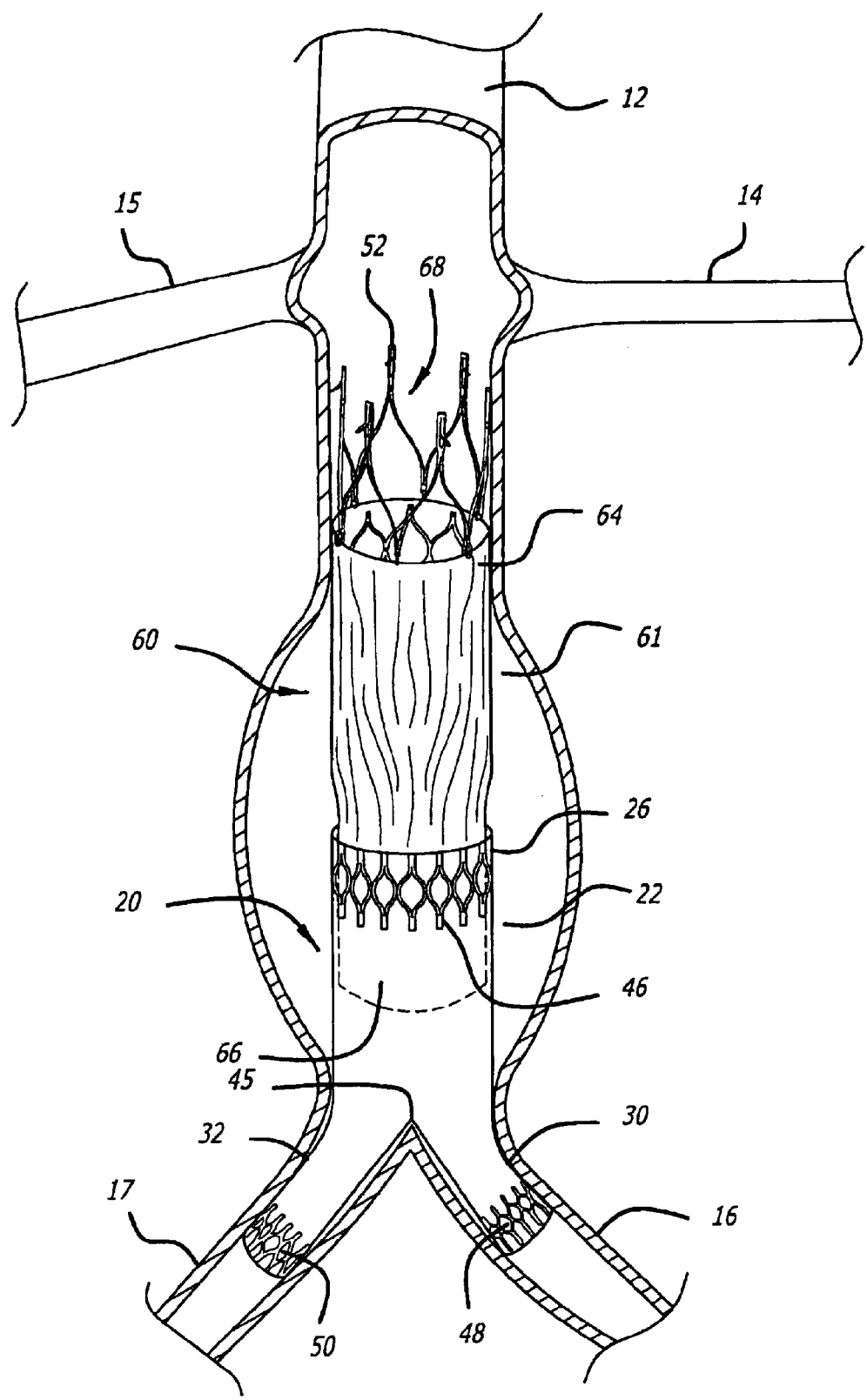
FIG. 9 is a partial cross-sectional view, showing the ends of the second element adopting different diameters.

The present invention may also accommodate inherent peculiarities or movements in the geometry of the patient's vasculature. While one patient's vasculature may present an aortic axis at the point of attachment of the tubular segment's superior end 64 which is aligned with the aortic axis at the point of attachment of the tubular section's inferior end 66, in other patients these axes may misaligned. In the latter case, it is therefore important that the tubular segment 61 be able to accommodate a certain misalignment between its ends. As exemplified in FIG. 8, the tubular segment 61 is adapted to accommodate such lack of axial alignment at its ends, in that the wall 62 is formed of material which will easily buckle, even when configured in a cylindrical profile, and thus will easily allow a bend to occur in the lumen of the tubular segment. Not only does this feature allow the use of the present invention in patients whose vasculature presents an awkward geometry, but it allows post-implantation movement to take place in the patient's vasculature without imposing disruptive forces on the fluid seals which may have been achieved between the graft and the vascular wall. An additional benefit to be derived from the flexibility of the wall 62 of the tubular segment 61 is that, even if it is fabricated to have a constant diameter from one end to the other in the pre-implanted condition, after attachment at both ends the second element 60 of the present invention may nevertheless accommodate a diameter at the superior end 64 which is different than the diameter at the inferior end 66. This feature allows the modular graft to accommodate the size of the vasculature despite pre-operative errors in measurement of the aortic diameter. For example, FIG. 9 exemplifies a modular bifurcated graft which, pre-operatively, was anticipated to require a tubular segment 61 having a cylindrical profile, yet which, after implantation, was found to require a diameter at its superior end 64 which is larger than the diameter at its inferior end 66. Due to its flexibility, the tubular segment 61 can accommodate this mismatch in size. Moreover, it is an advantage of the present invention that, even without error in pre-operative sizing of the patient's vasculature, a tubular segment 61 with cylindrical profile may be inserted between an aortic neck 12 having a certain diameter and a lumen of a docking section 22 having a different diameter, as may be dictated by the geometry of the vasculature. It is to be recognized that although FIG. 9 shows the fourth support structure 68 implanted within the aorta 12 inferior to the renal arteries 14, 15, the fourth support structure 68 can be positioned supra-renal with the superior end 64 of the second element 60 located just inferior the renal openings.

Thus, the configuration of the present invention provides a modular graft which minimizes problems associated with twisting, which derives resistance to inferior migration from the geometry of the vasculature, which has a substantial seal between its two modular elements, and which can accommodate unanticipated vascular geometries and post-implantation movement of the vasculature.

It will be apparent from the foregoing that, while particular forms of the invention have been illustrated and described, various modifications can be made without departing from the spirit and scope of the invention.

Accordingly, it is not intended that the invention be limited, except as by the appended claims.

I claim:

1. A method for repairing an aorta in an area proximate renal arteries and having a point of bifurcation, using a graft assembly including a first element and a second element, the first element having a bifurcation junction, first and second legs extending from the bifurcation junction, a support stent disposed distal to the bifurcation junction, and a plurality of leg support devices at least one of which is operatively associated with each of the first and second legs, the second element having a second element support structure attached thereto prior to placement of the second element in an aorta, comprising:

inserting the first element within the aorta;

configuring the bifurcation junction of the first element at the point of bifurcation of the aorta such that the graft spans and is supported by the point of bifurcation;

actuating the leg support devices to affix the first and second legs within the aorta;

attaching the second element to the first element subsequent to actuating the leg support devices to affix the first and second legs; and configuring the second element support structure to fixate the second element superior to the renal arteries by causing the second element support structure to directly engage and be in contact with the aorta so that the second element extends from contact with the first element to superior the renal arteries.

2. The method of claim 1, wherein the first element includes a docking site, further comprising:

attaching the second element to the docking site of the first element.

3. The method of claim 2, wherein the first element includes at least one bracing wire extending from one of the first and second limbs to the docking site for supporting the bifurcation junction of the first element.

4. The method of claim 2, wherein a diseased portion is located between the renal arteries and point of bifurcation, further comprising:

configuring the first element in the body lumen so that the docking site is free floating within the diseased portion.

5. The method of claim 2, further comprising overlapping the second element with the docking site of the first element to form a seal.

6. The method of claim 5, wherein the body lumen has a length, further comprising:

adjusting the seal of the second element with the docking site of the first element to span the length of the body lumen.

7. The method of claim 1, further comprising:

securing the second element inferior to the renal arteries.

8. The method of claim 1, wherein the second element includes an inner lumen, and a support system with hooks attached inside the inner lumen, further comprising:

actuating the support system so the hooks extend through the second element and into the aorta.

9. The method of claim 1, wherein the second element includes a superior and inferior end, and a support system with hooks attached to the superior end of the second, further comprising:

actuating the support system so the hooks are secured to the aorta.

10. The method of claim 1, wherein the second element is formed of a material that buckles to allow a bend to occur in the second element after attaching the second element to the first element in a body lumen that is curved or angled.

* * * * *